United States Patent
Beplate

(10) Patent No.: US 6,689,278 B2
(45) Date of Patent: Feb. 10, 2004

(54) COMBINED HYDROPHOBIC-HYDROPHILIC FILTER FOR FLUIDS

(76) Inventor: Douglas K. Beplate, 2254 Candlestick Ave., Henderson, NV (US) 89052

( * ) Notice: Subject to any disclaimer, the term of this patent is extended or adjusted under 35 U.S.C. 154(b) by 0 days.

(21) Appl. No.: 10/128,367

(22) Filed: Apr. 22, 2002

(65) Prior Publication Data

US 2003/0042211 A1 Mar. 6, 2003

Related U.S. Application Data

(63) Continuation-in-part of application No. 09/728,332, filed on Nov. 30, 2000, now Pat. No. 6,375,854, which is a continuation-in-part of application No. 09/345,201, filed on Jun. 30, 1999, now abandoned, which is a continuation of application No. 09/081,249, filed on May 19, 1998, now abandoned, which is a continuation of application No. 08/752,177, filed on Nov. 18, 1996, now abandoned.

(51) Int. Cl.$^7$ .............................................. B01D 29/56
(52) U.S. Cl. ..................... 210/767; 55/485; 55/488; 55/489; 210/323.1; 210/488; 210/489
(58) Field of Search ................... 210/767, 295, 210/323.1, 436, 472, 483, 488, 489, 496, 503; 55/315, 318, 482, 483, 485, 486, 488, 489

(56) References Cited

U.S. PATENT DOCUMENTS 4,938,389 A * 7/1990 Rossi et al. ............ 222/189.08
5,126,054 A * 6/1992 Matkovich .................. 210/641
5,536,413 A * 7/1996 Bormann et al. ........... 210/650

* cited by examiner

Primary Examiner—John Kim
(74) Attorney, Agent, or Firm—Thompson E. Fehr

(57) ABSTRACT

A combined filter for removing an aqueous fluid and entities, such as bacteria, existing in such aqueous fluid, from a nonaqueous fluid is described. The combined filter consists of a hydrophilic filter and a hydrophobic filter that are arranged in fluid communication and serially to be placed along the flow path of a fluid. The hydrophilic filter and the hydrophobic filter may touch one another or be located some distance from one another. Also, a structure may be inserted into the space between the hydrophilic filter and the hydrophobic filter that will maintain the space between the hydrophilic filter and the hydrophobic filter without significantly restricting the flow of fluid. And, in one embodiment, the combined filter may be composed simply of material having both hydrophilic and hydrophobic characteristics on the molecular level. Preferably, however, the filters and spacing structure are contained within an encasement having an inlet and an outlet. As any filter or spacer is located farther downstream with respect to the intended flow of fluid, the dimensions of that filter or spacer in the direction perpendicular to the intended flow of fluid decrease to a sufficient extent that, as the stream of fluid expands perpendicularly to its intended direction of flow, the possibility of the fluid contacting any solid element other than a filter is increased.

8 Claims, 3 Drawing Sheets

COMBINED HYDROPHOBIC-HYDROPHILIC FILTER FOR FLUIDS

CROSS-REFERENCE TO RELATED APPLICATION

This is a continuation-in-part of U.S. application Ser. No. 09/728,332, filed on Nov. 30, 2000, which will issue on Apr. 23, 2002 on U.S. Pat. No. 6,375,854 and which was a continuation-in-part of U.S. application Ser. No. 09/345,201, filed on Jun. 30, 1999, now abandoned, which was a continuation of U.S. application Ser. No. 09/081,249, filed on May 19, 1998, now abandoned, which was a continuation of U.S. application Ser. No. 08/752,177, filed on Nov. 18, 1996, now abandoned.

BACKGROUND OF THE INVENTION

1. Field of the Invention

This invention relates to a filter for removing an aqueous fluid and entities, such as bacteria, existing in such aqueous fluid, from a nonaqueous fluid.

2. Description of the Related Art

A number of patents are directed toward the combination of a hydrophobic filter and a hydrophilic filter for removing air or other gas from an intravenous fluid before such intravenous fluid reaches a patient. See, e.g., U.S. Pat. Nos. 4,013,072; 4,031,891; 4,116,646; 4,262,668; 4,278,084; 4,515,606; 4,525,182; 4,571,244; 4,615,694; 5,126,054; 5,308,333; 5,439,587; and 5,536,413.

None of the preceding patents, however, applies to a device which filters the fluid first through the hydrophobic filter and then through the hydrophilic filter or vice-versa. In each case, the intravenous liquid comes into contact with a hydrophobic filter through which gas from the liquid may escape and then the intravenous liquid passes through a hydrophilic filter.

Three patents do, though, apply to devices which transmit fluid through both a hydrophobic filter and a hydrophilic filter, viz., U.S. Pat. Nos. 4,026,792; 4,459,139; and 4,938,389.

U.S. Pat. No. 4,026,792 of George Otto Orth, Jr. applies to a "method of treating waste water containing particulate matter, liquid oils and fats to remove the same. . . ." The disclosure indicates that this waste water is first forced through a hydrophobic filter by centrifugal force. "Fats, oil and oily particulate matter are adsorbed by the hydrophobic filter . . . . The remaining waste water then moves radially into the hydrophilic filter . . . which removes the remaining particulate matter. As indicated in column 3 of U.S. Pat. No. 4,459,139, "The key characteristic of the hydrophobic filter membrane is, of course, that it will allow air or other gas to pass therethrough but will block the passage of water or other aqueous liquids. . . . [But] . . . a hydrophobic filter membrane has its own water-breakthrough point, i.e., the amount of pressure differential across the membrane required to drive water through it." For the method of U.S. Pat. No. 4,026,792 to function as intended, the centrifugal force must, therefore, be sufficiently large that the pressure differential at least equals the water-breakthrough point.

In U.S. Pat. No. 4,459,139 of Charles E. vonReis and Karlis Vizulis, itself, a device is claimed "having a hydrophilic filter in overlying relationship to [a] . . . hydrophobic filter on the inlet chamber side of the hydrophobic filter such that any fluid flow from the inlet chamber to the outlet chamber can only be by passage of the fluid first through the hydrophilic filter and then through the hydrophobic filter. . . " Both the hydrophobic filter and the hydrophilic filter have a pore size rating in air of less than 0.5 microns and, preferably, of approximately 0.2 microns; each then ". . . blocks bacteria from passing. . . . " These filters, furthermore, preclude liquid from reaching a suction pump used to aspirate liquid from a patient. The fact that a significant pressure differential is created across the combined filters is evident from the following excerpts:

In columns 2 and 3, it is stated that "[i]n operation the aspirator pulls a vacuum (i.e. a negative pressure) . . . to aspirate fluid from the patient. . . . "

The vonReis patent, in column 4, further observes, "The hydrophobic filter used in the practice of the present invention should preferably have a water-breakthrough point of at least about 10 psi, and ideally above the maximum pressure differential which can be expected, i.e. about 14 psi for the aspirating system described."

Columns 1 and 2 of the vonReis patent contain a declaration that, "[i]t is well known that a hydrophilic filter allows the passage of air therethrough until it is saturated with liquid but blocks or at least substantially restricts the passage of air when it does become saturated with liquid. Where the pressure differential across the hydrophilic filter does not exceed the bubble point of the filter (i.e. the pressure required to force air through the filter when it is saturated with liquid), the passage of air is completely blocked when it becomes saturated. But even where the pressure differential does exceed the bubble point, the hydrophilic filter when saturated will nevertheless substantially restrict the passage of air."

And, again in column 4 of the vonReis patent, one reads, " . . . in a preferred embodiment the hydrophilic filter membrane used had a bubble point of from about 7 to 10 psi and as it reached saturation the blockage of air was about 80%. . . . ".

U.S. Pat. No. 4,525,182 of Donald B. Rising and Richard G. Naegeli, Jr., in fact, asserts, "The typical small pore size of the wetted [hydrophilic] filter prevents gas from passing through said filter at the usual operating pressures." Moreover, using almost identical language, U.S. Pat. No. 5,439,587 of Ralph J. Stankowski, Michael C. Heath, and Douglas A. Boucher asserts, "The typical small pore size of the hydrophilic filter prevents gas from passing through the filter at the usual operating pressures."

The third patent concerning a device which transmits fluid through both a hydrophobic filter and a hydrophilic filter, i.e., U.S. Pat. No. 4,938,389 of Scott R. Rossi and Jeffrey P. Gilbard, claims a reservoir for storing sterile liquids connected to a dispensing tip with a flow passage across which a filter assembly is sealed. The filter assembly comprises "a hydrophilic filter and a hydrophobic filter arranged in fluid communication serially along said flow passage so that said hydrophilic filter is nearer to said reservoir than said hydrophobic filter, said hydrophobic filter and said hydrophilic filter each having pores sufficiently small to act as a microbial filters."

"In preferred embodiments of the invention, the filter assembly has the hydrophobic and hydrophilic filters separated, e.g., by a support ring. A more preferred embodiment has a filter structure whereby there are a plurality of support rings between, and on opposite sides of, the filters to provide structural support and filter separation."

Since the examples of the Rossi patent utilized an "eye drop solution" as the sterile liquid, since solutions for rinsing a person's eyes are generally aqueous saline solutions, and since the Rossi patent was not limited to nonaqueous solutions, it is apparent that a significant pressure differential would have to be created across the hydrophobic filter, i.e., the water-breakthrough point would have to be reached, in order to permit the solution to pass through the hydrophobic filter.

It should be noted that none of the preceding patents were intended to remove water from another liquid.

Additionally, lines 11 through 12 in column 3 of U.S. Pat. No. 5,126,054 clarify that the "[l]iquiphobic layer 18 is superimposed on liquiphilic layer 16. . . . " Similarly, U.S. Pat. No. 5,536,413 implies that there is no space between the liquiphobic and the liquiphilic layers of the gas venting element of that patent when it states that " . . . the layers of the gas venting element may be individually prepared and bonded together by various means known to those skilled in the art."

Moreover, none of the filter material in the preceding patents combines hydrophilic and hydrophobic characteristics on the molecular level. U.S. Pat. No. 4,031,891 of Thurman S. Jess does state, "While the invention has been described above as using three different filter elements, namely a hydrophilic filter element to cover the central window opening . . . and separate hydrophobic filter elements covering the opposing window openings . . . , it will be understood by those skilled in the art that use can also be made of a continuous sleeve of filter material, the ends of which have been rendered hydrophobic in nature and the central portion of which has been rendered hydrophilic in nature." It is, however, apparent that the hydrophilic and the hydrophobic segments of the filter in the Jess patent are distinct from one another on a macroscopic level. This is, also, true for the filter material to which reference is made in U.S. Pat. No. 4,278,084 of J. Lee Pope, Jr.: " . . . it has been suggested in U.S. Pat. No. 3,520,416 to Keedwell to use a microporous filter material which is hydrophilic in some areas, and hydrophobic, as by the application of silicone treatment, in other areas."

SUMMARY OF THE INVENTION

The present invention consists of a hydrophilic filter and a hydrophobic filter arranged in fluid communication serially along the flow path of a fluid.

In a first embodiment the pores of both the hydrophilic filter and of the hydrophobic filter are selected to be of such a size that bacteria can not pass through either filter but that a gas such as air can substantially freely traverse the filters.

In a second embodiment the pores can be larger since it is merely desired to prevent an aqueous fluid, such as water, in a nonaqueous fluid, such as gasoline, from passing through the filters with the nonaqueous fluid.

In both embodiments, the hydrophilic filter and the hydrophobic filter could touch one another, but it is preferred to maintain a space between them to accommodate any of the fluid which is desired to be removed that manages to pass the first filter in the flow path but not the second filter. It is, furthermore, preferred to place within such space a structure that will maintain the space between the hydrophilic filter and the hydrophobic filter without significantly restricting the flow of fluid. This facilitates drying of any fluid between the hydrophobic filter and the hydrophilic filter.

In fact, preferably an encasement having an inlet and an outlet contains the hydrophilic and the hydrophobic filters and possesses a spacer to maintain the hydrophobic filter physically separate from the hydrophilic filter. The hydrophilic filter is preferably placed so that in use it will be upstream from the hydrophobic filter. As the encasement, filters, and spacer proceed in the direction that is intended to be downstream, the dimensions of the filters and spacer perpendicular to the intended direction of fluid flow decrease so that as the stream of fluid expands perpendicularly to its intended direction of flow, the possibility of the fluid contacting other than a filter and thereby precipitating some of any aqueous liquid that the fluid may contain is increased.

And an additional embodiment is composed of filter material which has both hydrophilic and hydrophobic characteristics on the molecular level.

DESCRIPTION OF THE PREFERRED EMBODIMENT

Figure 1:
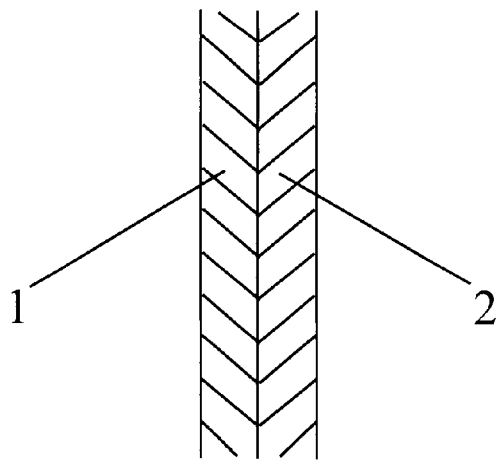
FIG. 1 illustrates the embodiment of the Combined Hydrophobic-Hydrophilic Filter for Fluids wherein the hydrophilic filter touches the hydrophobic filter.

The Combined Hydrophobic-Hydrophilic Filter for Fluids, in a first embodiment, comprises, as depicted in FIG. 1, a hydrophilic filter 1 and a hydrophobic filter 2 that are arranged in fluid communication and serially to be placed along the flow path of a fluid.

When the Combined Hydrophobic-Hydrophilic Filter for Fluids is to be utilized to remove an aqueous fluid, such as water, from a gas, such as air, the pores in both the hydrophilic filter 1 and the hydrophobic filter 2 are preferably selected to be of such a size that bacteria can not pass through either filter but that a gas, such as air, can substantially freely traverse both the hydrophilic filter 1 and the hydrophobic filter 2.

When, however, the Combined Hydrophobic-Hydrophilic Filter for Fluids is to be used to prevent an aqueous fluid, such as water, in a nonaqueous fluid, such as gasoline, from passing through the filters with the nonaqueous fluid, the pores can be larger.

Figure 2:
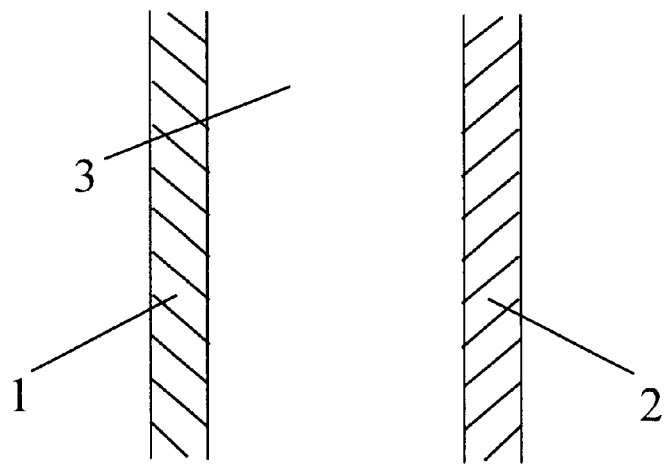
FIG. 2 portrays the embodiment which has a space between the hydrophilic filter and the hydrophobic filter.

If one desires not only to preclude the passage of an aqueous fluid, but also to remove such aqueous fluid from a nonaqueous fluid, it is preferable—as illustrated in FIG. 2—to have the hydrophilic filter 1 located some distance from the hydrophobic filter 2 in order to create a space 3 within which any on the aqueous fluid which manages to pass the upstream filter may collect. It is, moreover, preferable to have the hydrophilic filter 1 as the upstream filter because the aqueous fluid will then either be absorbed into the hydrophilic filter 1 or pass into the space 3 where it will remain because its further travel will be precluded by the hydrophobic filter 2. When a significant quantity of aqueous fluid collects within the space 3, either such aqueous fluid can be removed from space 3 or the entire Combined Hydrophobic-Hydrophilic Filter for Fluids can be removed from the flow path of a fluid and replaced with another Combined Hydrophobic-Hydrophilic Filter for Fluids.

Figure 3:
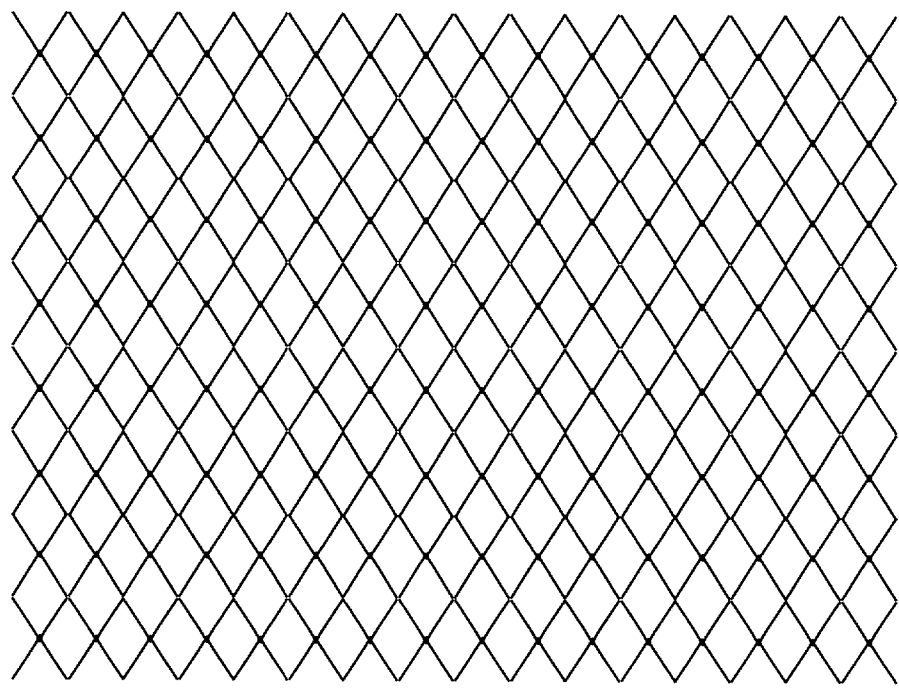
FIG. 3 shows a honeycomb structure from above, which honeycomb structure is placed between the hydrophilic filter and the hydrophobic filter to maintain a space between the hydrophilic filter and the hydrophobic filter without significantly restricting the flow of fluid.

In some circumstances it is desirable to maintain the space 3 between the hydrophilic filter 1 and the hydrophobic filter 2 by inserting into the space 3 a structure that will maintain the space between the hydrophilic filter and the hydrophobic filter without significantly restricting the flow of fluid, such as the honeycomb material depicted in FIG. 3.

Figure 4:
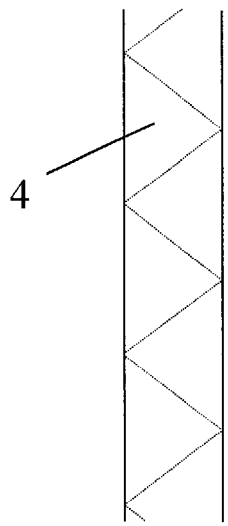
FIG. 4 depicts the Combined Hydrophobic-Hydrophilic Filter for Fluids wherein a filter material is utilized which has both hydrophilic and hydrophobic characteristics on the molecular level.

In other circumstances it will be desirable to utilize as the Combined Hydrophobic-Hydrophilic Filter for Fluids material 4 having both hydrophilic and hydrophobic characteristics on the molecular level, as illustrated in FIG. 4.

Figure 5:
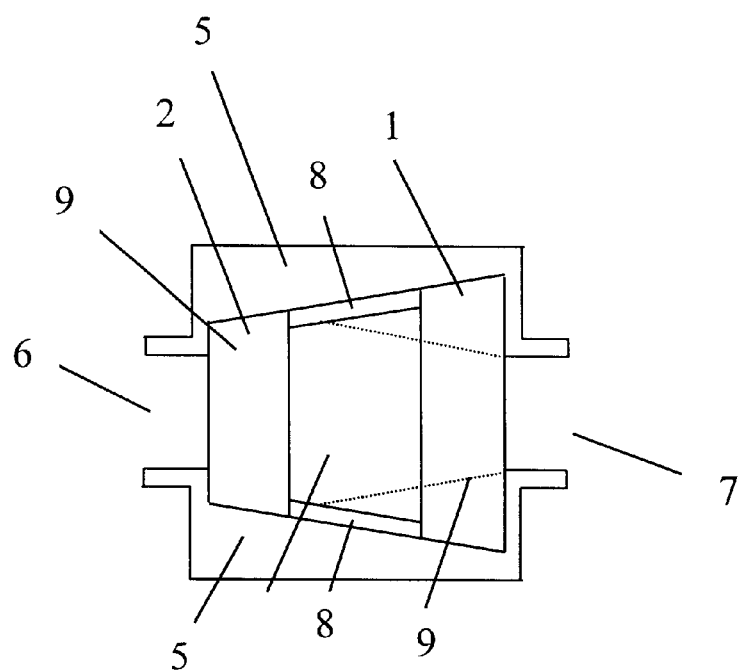
FIG. 5 is a cutaway view from the side of the encasement containing the hydrophobic filter, the hydrophilic filter, and the spacer.
Figure 6:
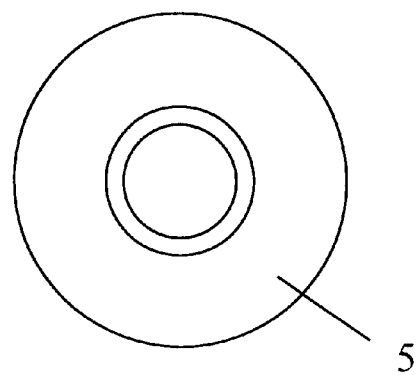
FIG. 6 shows a view from either end of the encasement containing the hydrophobic filter, the hydrophilic filter, and the spacer.

A preferred structure for the Combined Hydrophobic-Hydrophilic Filter for Fluids utilizes, as illustrated in FIG. 5, an encasement 5 having an outlet 6 and an intlet 7. The encasement 5 contains one or more hydrophilic filters 1 and one or more hydrophobic filters 2. A spacer 8 located between the hydrophilic filter or filters 1 and the hydrophobic filters 2 maintains the space 3 by keeping the hydrophilic filters 1 physically separate from the hydrophobic filters 2. As discussed above, the hydrophilic filter or filters 1 are preferably placed so that in use the hydrophilic filter or filters 1 will be upstream from the hydrophobic filter or filters 2. And as the filters 1, 2 and spacer 8 are located farther in the direction that is intended to be downstream, the dimensions of the filters 1, 2 and spacer 8 perpendicular to the intended direction of fluid flow decrease to a sufficient extent that, as the stream of fluid 9 expands perpendicularly to its intended direction of flow, the possibility of the fluid contacting any solid element other than a filter 1, 2 and thereby precipitating some of any aqueous liquid that the fluid may contain, is increased.

There are, of course, many applications for the Combined Hydrophobic-Hydrophilic Filter for Fluids. One is as a surgical mask or the similar mask worn by those who must be in an environment contaminated with germs or dust. Another is as a device to remove contaminants from the air which is recirculated within an airplane.

An example of the Combined Hydrophobic-Hydrophilic Filter for Fluids utilized to remove bacteria from air is:

EXAMPLE

Heat and Moisture Exchange Media (HME), which is commercially available from 3M Filtration Products of St. Paul, Minn., was used for the hydrophilic filter; and Filtrete Air Filter Media Type S, which is, also, commercially available from 3M Filtration Products of St. Paul, Minn., was utilized for the hydrophobic filter.

Five filters were tested. The differential pressure across each filter, utilizing an air flow of 8 liters per minute, was 14.5 mm $H_2O$ for Filter no. 1, 15.2 mm $H_2O$ for Filter no. 2, 17.5 mm $H_2O$ for Filter no. 3, 14.7 mm $H_2O$ for Filter no. 4, and 15.5 mm $H_2O$ for Filter no. 5.

A test procedure was conducted to determine the Bacterial Filtration Efficiency (BFE), a ratio of (a) the difference between the number of colony forming units (CFU) in the challenge delivered to the filter and the number of colony forming units in the sample tested after passage through the filter to (b) the number of colony forming units (CFU) in the challenge delivered to the filter.

$$BFE\ \% = \frac{C-T}{C} \times 100$$

where C is the average control value for the number of colony forming units (CFU) in the challenge delivered to the filter, and T is the number of colony forming units in the sample tested after passage through the filter.

A culture of *Staphylococcus aureus* was diluted in 1.5% peptone water to a precise concentration to yield challenge level counts of 2200±500 colony forming units per test sample. The bacterial culture suspension was pumped through a "Chicago" nebulizer at a controlled flow rate and fixed air pressure. The constant challenge delivery, at a fixed air pressure, formed aerosol droplets with a mean particle size of approximately 3.0 $\mu$m. The aerosol droplets were generated in a glass aerosol chamber and drawn through a six-stage, viable particle Andersen sampler for collection. The sampler was maintained at 28.3 liters per minute (1 cubic foot per minute). Test controls and test samples were challenged for a two-minute interval.

The delivery rate of the challenge also produced a consistent challenge level of 2200±500 CFU on the test control plates. A test control (which had no filter in the airstream) and reference material were included after 7 to 10 test samples. The Andersen sampler, a sieve sampler, impinged the aerosol droplets onto six agar plates based on the size of each droplet. The agar medium used was soybean casein digest agar (SCDA). The agar plates were incubated at 37° C.±2° C. for 48±3 hours. The colonies formed by each bacteria-laden aerosol droplet were then counted and convert to "probable-hit" values using the hole conversion chart provided by Andersen.

Each of the five filters achieved a BFE exceeding 99.9 percent. In fact, there were no detected colonies on any of the Andersen sampler plates for Filter no. 1, Filter no. 3, and Filter no. 4.

It should, moreover, be noted that the test procedure utilized produces a more severe challenge to most filtration materials than would be expected in normal use.

I claim:

1. A combined hydrophobic-hydrophilic filter for fluids, which comprises:
- an encasement having an inlet and an outlet;
- one or more hydrophilic filters;
- one or more hydrophobic filters arranged in fluid communication and serially with said hydrophilic filters; and
- a spacer located between said hydrophilic filter or filters and said hydrophobic filter or filters, wherein the dimensions of said filter or filters and said spacer perpendicular to the intended direction of fluid flow decrease the farther such filter or filters and said spacer are located downstream with respect to the intended direction of fluid flow to a sufficient extent that, as the stream of fluid expands perpendicularly to its intended direction of flow, the possibility of the fluid contacting any solid element other than a filter is increased.

2. The combined hydrophobic-hydrophilic filter for fluids as recited in claim 1, wherein:
- the pores of both said one or more hydrophilic filters and said one or more hydrophobic filters are selected to be of such a size that bacteria can not pass through either the hydrophilic filter or the hydrophobic filter but that a gas can substantially freely traverse both the hydrophilic filter or filters and the hydrophobic filter or filters.

3. The combined hydrophobic-hydrophilic filter for fluids as recited in claim 2, wherein:
- said hydrophilic filter or filters are located so that in use said hydrophilic filter or filters will be upstream with respect to the intended direction of fluid flow from said hydrophobic filter or filters.

4. The combined hydrophobic-hydrophilic filter for fluids as recited in claim 1, wherein:
- said hydrophilic filter or filters are located so that in use said hydrophilic filter or filters will be upstream with respect to the intended direction of fluid flow from said hydrophobic filter or filters.

5. A process for removing an aqueous fluid from being combined with a nonaqueous fluid, which comprises:

causing the combined fluids to enter the inlet of an encasement;

causing the combined fluids to flow through one or more hydrophilic filters within such encasement, which one or more hydrophilic filters will absorb the aqueous fluid;

causing the combined fluids to encounter a hydrophobic filter, which hydrophobic filter will not permit the aqueous fluid to pass but which will allow the nonaqueous fluid to flow through the hydrophobic filter;

maintaining such hydrophilic filter or filters physically apart from such hydrophobic filter or filters with a spacer; and having the dimensions of the hydrophilic filter or filters, the hydrophobic filter or filters, and the spacer perpendicular to the intended direction of fluid flow decrease the farther the hydrophilic filter or filters, the hydrophobic filter or filters, and the spacer are located downstream with respect to the intended direction of fluid flow to a sufficient extent that, as the stream of fluid expands perpendicularly to its intended direction of flow, the possibility of the fluid contacting any solid element other than a filter is increased.

6. The process for removing an aqueous fluid from being combined with a nonaqueous fluid as recited in claim 5, further comprising:

selecting the pores of both the one or more hydrophilic filters and the one or more hydrophobic filters to be of such a size that bacteria can not pass through either the hydrophilic filter or the hydrophobic filter but that a gas can substantially freely traverse both the hydrophilic filter or filters and the hydrophobic filter or filters.

7. The process for removing an aqueous fluid from being combined with a nonaqueous fluid as recited in claim 6, further comprising:

locating the hydrophilic filter or filters so that in use the hydrophilic filter or filters will be upstream with respect to the intended direction of fluid flow from the hydrophobic filter or filters.

8. The process for removing an aqueous fluid from being combined with a nonaqueous fluid as recited in claim 5, further comprising:

locating the hydrophilic filter or filters so that in use the hydrophilic filter or filters will be upstream with respect to the intended direction of fluid flow from the hydrophobic filter or filters.

* * * * *